United States Patent
Gemmel et al.

(10) Patent No.: US 10,706,546 B2
(45) Date of Patent: Jul. 7, 2020

(54) METHOD FOR OPERATING A MEDICAL IMAGING DEVICE AND A MEDICAL IMAGING DEVICE

(71) Applicant: Siemens Healthcare GmbH, Erlangen (DE)

(72) Inventors: Alexander Gemmel, Erlangen (DE); Gerhard Kleinszig, Forchheim (DE); Björn Kreher, Bräuningshof (DE); Holger Kunze, Bubenreuth (DE); Jessica Magaraggia, Erlangen (DE); Stefan Schneider, Erlangen (DE); Markus Weiten, Nürnberg (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/442,725

(22) Filed: Jun. 17, 2019

(65) Prior Publication Data

US 2019/0392582 A1    Dec. 26, 2019

(30) Foreign Application Priority Data

Jun. 26, 2018    (EP) .................................. 18179804

(51) Int. Cl.
```
A61B 6/00      (2006.01)
G06T 7/00      (2017.01)
G16H 30/40     (2018.01)
G06T 11/00     (2006.01)
G06T 15/08     (2011.01)
```

(52) U.S. Cl.
CPC .......... *G06T 7/0016* (2013.01); *A61B 6/4405* (2013.01); *A61B 6/4441* (2013.01); *A61B 6/542* (2013.01); *G06T 11/008* (2013.01); *G06T 15/08* (2013.01); *G16H 30/40* (2018.01); *G06T 2207/10116* (2013.01); *G06T 2207/20081* (2013.01); *G06T 2207/20084* (2013.01); *G06T 2207/30008* (2013.01); *G06T 2211/424* (2013.01); *G06T 2211/428* (2013.01)

(58) Field of Classification Search
CPC ........ G06K 9/00; G06F 19/321; G06F 19/345
USPC ........................................... 382/131
See application file for complete search history.

(56) References Cited

U.S. PATENT DOCUMENTS

| | | | |
|---|---|---|---|
| 2017/0011185 A1* | 1/2017 | Schweizer | ............ G06F 19/321 |
| 2018/0061059 A1 | 3/2018 | Xu | |
| 2018/0116620 A1 | 5/2018 | Chen | |

FOREIGN PATENT DOCUMENTS

| | | |
|---|---|---|
| DE | 102015212953 A1 | 1/2017 |
| EP | 3316217 A1 | 5/2018 |

OTHER PUBLICATIONS

European Search Report for European Patent Application No. 18179804.2-1124 dated Jan. 10, 2019, with English Translation..

* cited by examiner

*Primary Examiner* — Abolfazl Tabatabai
(74) *Attorney, Agent, or Firm* — Lempia Summerfield Katz LLC

(57) ABSTRACT

A method is provided for operating a medical imaging device when performing an imaging examination. In order to allow an improved preparation of images in the context of such an imaging examination, the method includes: providing an original image of a body region; recording an updated image of the body region; and generating a three-dimensional subsequent image from the original image and from the updated image using a previously trained artificial neural network.

15 Claims, 2 Drawing Sheets

METHOD FOR OPERATING A MEDICAL IMAGING DEVICE AND A MEDICAL IMAGING DEVICE

The present patent document claims the benefit of European Patent Application No. EP 18179804.2, filed Jun. 26, 2018, which is also hereby incorporated by reference.

TECHNICAL FIELD

The disclosure relates to a method for operating a medical imaging device when carrying out an imaging examination. A second aspect of the disclosure relates to a medical imaging device.

BACKGROUND

Examples of imaging devices are X-ray devices, computed tomography devices, and magnetic resonance tomography devices. The imaging examination may therefore include an X-ray examination, computed tomography, and/or magnetic resonance tomography. Such imaging examinations are carried out, for example, to generate images of a body region of a patient. Such images may be used for a surgical intervention, the imaging examination being independent of the surgical intervention. For example, the imaging examination is carried out before, after, and/or in intermediate phases of the surgical intervention. The present method relates to the technical evaluation of raw data or pre-processed data relating to the medical imaging device, in order to provide the aforementioned images of the body region.

For example, such an imaging examination may be used to support a surgical intervention to treat a bone fracture. In this case, the images may be generated using the imaging method before, after, or during the surgical intervention to treat the bone fracture or a broken bone. By the imaging examination, a physician who is carrying out the surgical intervention may obtain a three-dimensional view over an anatomy of the bone fracture and/or of medical objects or implants that have been inserted. Taking a 3D image during the surgical intervention is elaborate, combined with a high radiation exposure, and it is not possible for many body regions. In particular, a 3D X-ray examination with a mobile X-ray device, (e.g., a C-arm device), additionally involves a large time input. Continuous 3D images are not possible.

The surgeon obtains the three-dimensional view by acquiring individual two-dimensional projection images. Yet, the informative value of the three-dimensional view, in particular, depends on the physician skillfully selecting respective projection directions for the individual projection images. Through a repeated preparation of such projection images for different projection directions and positions of the mobile X-ray device, the three-dimensional view may be expanded or completed. The number of necessary projection images for this depends heavily on the ability and experience of the physician. Each additional projection image leads to a lengthening of an operating time for the surgical intervention and to an increase in the radiation dose for the patient.

SUMMARY AND DESCRIPTION

The present disclosure addresses the problem of allowing an improved provision of images in the context of a class-specific imaging examination.

The scope of the present disclosure is defined solely by the appended claims and is not affected to any degree by the statements within this summary. The present embodiments may obviate one or more of the drawbacks or limitations in the related art.

A first aspect of the disclosure relates to a method for operating a medical imaging device when carrying out an imaging examination. The method includes the following acts: providing an original image of a body region; recording an updated image of the body region; and generating a three-dimensional subsequent image from the original image and from the updated image using a previously trained artificial neural network.

The original image of the body region may be a previously recorded projection image of the body region. Consequently, the three-dimensional subsequent image may be generated from the original image, (e.g., from the projection image), and from the X-ray image using the artificial neural network. When providing the original image, a plurality of original images may be provided, which in the context of the present method, may be processed in the same way as an individual original image. In particular, the plurality of original images has different projection directions in relation to the body region.

The updated image may be a two-dimensional projection image. The updated image may be an X-ray image, advantageously a two-dimensional X-ray image. The X-ray image may be recorded using a mobile X-ray device, (e.g., using a C-arm device). Alternatively, the updated image may be recorded using an ultrasound device, a magnetic resonance tomography device, an optical video camera, or any other imaging device. Accordingly, the updated image may be an ultrasound image, a magnetic resonance tomography image, or a video image.

The updated image is, in particular, not recorded in the context of an image sequence that is carried out to generate a three-dimensional representation. Therefore, in the case of a plurality of updated images, these images may be any images with any representation of the body region.

The original image may be recorded using a different imaging method or a different imaging device than the updated image. In this case, provision may be made for the medical X-ray device to receive the original image from a further medical imaging device and subsequently provide it for further processing. The images recorded with different imaging methods or with different imaging devices, (e.g., the original image and the updated image), may then be further processed into the three-dimensional subsequent image. In other words, the three-dimensional subsequent image is generated from the aforementioned images. It is also possible, however, for the original image and the updated image to be recorded using the same imaging method and/or using the same imaging device. Accordingly, the original image may be recorded using a mobile X-ray device, (e.g., a C-arm device). In this case, in particular, a plurality of original images is recorded so that three-dimensional information relating to the body region is already provided by these images.

The body region may be a part of the (e.g., human) skeleton. For example, the body region is an individual bone, a plurality of bones, or a joint. Alternatively, the body region may be soft tissues in the (e.g., human) body, for example, a lung, liver, blood vessels, or digestive tract. In the case of soft tissues, the distribution of a contrast agent may be visualized by the method. In summary, by the present method, soft tissues, bones, or joints, for example, may be examined. Yet any other body regions are also conceivable. Moreover, the method is not restricted to the human body.

Provision may be made in the process act that involves recording the updated image for a plurality of updated images to be recorded. The plurality of updated images is all processed, in particular, in the same way as the updated image. In particular, the plurality of updated images includes different projection directions in relation to the body region.

The artificial neural network may be trained such that the three-dimensional subsequent image may be generated from the original image and the updated image by the artificial neural network. The more comprehensively the artificial neural network has been trained, the more precisely the three-dimensional subsequent image may be generated. In particular, for generating the three-dimensional subsequent image, the more comprehensively the artificial neural network is trained, the fewer original images or updated images are required. When training the artificial neural network, this may be equipped with prior knowledge relating to the generation of a three-dimensional representation of an anatomy using updated images and/or original images. This prior knowledge may be used by the artificial neural network to generate a three-dimensional subsequent image. The three-dimensional subsequent image is, in particular, a three-dimensional representation of the body region. In particular, the artificial neural network is or becomes trained to use one or a plurality of updated images in connection with an original image to generate the three-dimensional subsequent image, the three-dimensional subsequent image and the one or a plurality of updated images not being in any pre-determined relationship with one another. In the case of a plurality of updated images, the artificial neural network may become or be trained to generate the three-dimensional subsequent image from the original image and the plurality of updated images. Not being in any pre-determined relationship with one another means, in particular, that the respective images, as described in the aforementioned, are not part of a pre-determined image sequence for generating a three-dimensional representation. In other words, the artificial neural network is advantageously trained to use an original image (e.g., original images), and an updated image (e.g., updated images) of the body region, which are in any relationship with one another to generate the three-dimensional subsequent image.

It may be advantageous to use the imaging parameters in the updated image to generate the subsequent image. For example, the updated image is a projection image, (e.g., an X-ray image), which is recorded using a mobile X-ray device, (e.g., a C-arm X-ray device). In this example, the imaging parameters may include one or a plurality of the following: recording direction (e.g., angular, orbital, and the C-arm orientation), C-arm position, acceleration voltage, amperage (e.g., tube current), charge (e.g., in product of the current strength and exposure time), and beam geometry. The imaging parameters may be used by the artificial neural network to generate the three-dimensional subsequent images. In particular, the artificial neural network may be trained or have relevant prior knowledge in order to use the imaging parameters to generate the three-dimensional subsequent images in an improved manner.

According to a development, provision is made for a three-dimensional original image of the body region to be provided as the original image. The three-dimensional original image is, in particular, a three-dimensional representation of the body region. The updated image may, as described in the aforementioned, be a two-dimensional updated image, advantageously a two-dimensional X-ray image. Provision is therefore made, when generating the three-dimensional subsequent image, for the three-dimensional subsequent image to be generated from the three-dimensional original image and from the two-dimensional updated image, in particular, from the X-ray image. In other words, according to this embodiment, first a three-dimensional original image and second a two-dimensional X-ray image are used or processed together to generate the three-dimensional subsequent image. This makes it possible using the artificial neural network for different dimensional images (two-dimensional and three-dimensional) to be processed together.

According to a development, provision is made such that the X-ray image represents the body region at a later time than the original image. In other words, the updated image may be more up to date than the original image. In this way, an information content of the original image and of the updated image may be blended together in a particularly advantageous manner. For example, through the artificial neural network, information relating to a spatial structure of the body region from the original image may be merged with up to date position-related information, for example, for a bone or a medical object, from the updated image. In this way, the three-dimensional subsequent image may be generated in a particularly advantageous manner based on one or few updated images.

According to a development, provision is made for the original image to be generated in the context of a computed tomography image and the recording of the X-ray image ensues using a mobile X-ray device, in particular, using a C-arm X-ray device. In other words, in this case, the updated image is an X-ray image. In the present example, the original image is a three-dimensional representation or a three-dimensional reconstruction of the body region. The computed tomography image may characterize the site in the body prior to a surgical intervention. On the other hand, the updated image may characterize the body region during the surgical intervention or during an intermediate phase in the surgical intervention. Therefore, the original image, which characterizes the body region prior to the surgical intervention, may be merged with the updated image, which characterizes the body region during the surgical intervention, to generate the three-dimensional subsequent image. In this way, on the one hand comprehensive earlier three-dimensional information may be merged with two-dimensional updated images, in particular, X-ray images. As a result, through the evaluation of the three-dimensional original image, the need for current updating images in order to generate the three-dimensional subsequent image as a current three-dimensional representation of the body region may be reduced.

According to a development, provision is made when generating the three-dimensional subsequent image, for the original image, (e.g., three-dimensional image), of the body region to be at least partly updated using the X-ray image. For example, a three-dimensional representation that is provided by the original image is at least partly updated using the more up to date image. Here, based on the prior knowledge of the previously trained artificial neural network, the current image information may be merged with the comprehensive three-dimensional information in the original image. The three-dimensional subsequent image or the three-dimensional representation of the body region that has been provided by the three-dimensional subsequent image may be updated using the updated image or using a plurality of updated images. For example, structural changes compared with the original image may be detected using the updated image, and the original image may be adjusted accordingly to generate the three-dimensional subsequent image. In this way, even with few updated images, a reliable and up to date three-dimensional representation may be provided in the form of the three-dimensional subsequent image.

In particular, provision is made for the original image and the updated image to characterize the body region during different phases in the same surgical intervention. For example, provision is made for the original image recorded during a previous phase in the surgical intervention to be compared with the updated image. For example, the original image may be acquired during a preliminary examination before the start of the surgical intervention. Then the updated image may be recorded during the surgical intervention. Examples of different phases in a surgical intervention to treat a bone fracture include preliminary examination to assess damage and select an entry point to the bone fracture, setting the bone fracture, clamping of reset bone fragments, and final fixing of the bone fragments using screws and/or pins. Therefore, it is possible in a practical example for the original image to be generated in a preliminary examination and for the updated images to be recorded during setting, clamping, and/or fixing. For example, a plurality of updated images is recorded during previous phases or during those listed by way of example. In this way, images of previous phases in a surgical intervention may be used to generate or provide the subsequent image of the body region for a later phase in the surgical intervention. The artificial neural network has in this case been trained to use updated images to generate the subsequent image.

According to a development, provision is made for the artificial neural network to be trained specifically in one of the different phases. For example, a trained artificial neural network is provided for each of a plurality of different phases. For example, an artificial neural network that is specifically trained in the setting phase is provided. For example, a different artificial neural network that is specifically trained in the clamping and/or fixing phase is provided. For example, in an additional process act, the artificial neural network that is trained in the current phase may be selected from a plurality of artificial neural networks. In this way, any respective prior knowledge that is generated by training the artificial neural network may be particularly well adjusted to the respective current phase.

According to a development, provision is made for a structural change in the body region that has occurred between the original image and the updated image to be determined and to be accounted for when generating the three-dimensional subsequent image. For example, it is determined in a targeted manner as to what has changed in the updated image compared with the original image. This may then be accounted for when updating the original image using the updated image. In particular, the structural change may be reproduced by moving image components in the original image. For example, this may be carried out in the manner of movement compensation for a movement that has occurred in the body region between the original image and the updated image.

According to a development, provision is made for a change in position of a bone fragment and/or of a medical object in the body region to be determined as the structural change. Examples of medical objects are clips, pins, and screws for fixing bone fragments in the body region. Bone fragments and/or medical objects may be moved in the context of the surgical intervention and/or arranged in the body region. This may result in an aforementioned change in position. This change in position is determined in the context of the present method. Moving of bone fragments and/or insertion of medical objects is not part of the method. The different phases in the surgical intervention, the performance whereof, and of the surgical intervention itself are not part of the method. The change in position of the bone fragment and/or of the medical object may be accounted for by the artificial neural network to generate the three-dimensional subsequent image using the original image. In particular, the change in position is accounted for to update the three-dimensional original image using the artificial neural network.

According to a development, provision is made, in order to account for the structural change, for the change in position of the bone fragment and/or of the medical object to be determined and accounted for by moving a representation of the bone fragment or of the medical object in the original image. In other words, the change in position is accounted for by moving the representation of the bone fragment or of the medical object in the original image. Therefore, in the original image, the representation of the bone fragment or of the medical object may be moved. This move may ensue, in particular, according to the predetermined change in position. In other words, the representation of the bone fragment or of the medical object in the original image may be moved into a current position in relation to the body region, which position has been acquired using the updated image. This is advantageous, in particular, when the original image is a three-dimensional original image. If the original image is a two-dimensional original image, then the generation of the three-dimensional subsequent image using the original image and the updated image may be made possible only by updating the original image, because to generate the three-dimensional representation of the body region, the position of the bone fragment and/or of the medical object in relation to the body region concurs in the original image and in the updated image.

According to a development, provision is made for the three-dimensional subsequent image to be generated iteratively, wherein in a subsequent iteration act, the three-dimensional subsequent image is used as a new original image and a new three-dimensional subsequent image is generated together with a new updated image. In other words, provision may be made for updated images to be recorded repeatedly and for a respective three-dimensional subsequent image to be generated from the respective updated images and from a respective original image. Here, each of the three-dimensional subsequent images serves, in particular, iteratively, as a new original image to generate the respective three-dimensional subsequent image. A three-dimensional item of information, which is provided by the three-dimensional subsequent image, or a precise detail of the three-dimensional subsequent image may therefore be improved iteratively using the consecutive updated images.

According to a development, provision is made for a plurality of original images to be provided and/or for a plurality of X-ray images to be recorded, wherein the three-dimensional subsequent image is generated from the plurality of original images and/or from the plurality of X-ray images. In other words, a plurality of original images may be provided as the original image. Alternatively, or additionally, a plurality of updated images may be recorded as the updated image. The three-dimensional subsequent image may be generated either from a plurality of original images and from an updated image, from an original image, and with a plurality of updated images, or from a plurality of original images and from a plurality of updated images. For example, in an iteration act in the iterative method, a plurality of updated images may be recorded as the updated image and the three-dimensional subsequent image generated therefrom within the one iteration act. In a subsequent iteration act, a plurality of updated images may be recorded in turn and the new three-dimensional subsequent image may be generated therefrom. In the case of a plurality of updated images, these images are advantageously recorded in each case during the same phase of the surgical intervention. In this way, the processing effort in the case of a plurality of updated images or of a plurality of original images may be reduced.

According to a development, provision is made for the artificial neural network to be at least partly trained using test images. The test images may be updated images of bone fractures, in particular, from earlier imaging examinations (e.g., X-ray images of earlier X-ray examinations), and/or may contain simulated X-ray images generated using a three-dimensional representation of a bone fracture. In addition, the test images may include updated images, (e.g., X-ray images), of artificially generated bone fractures, (e.g., in human bodies released for medical research). For example, the artificial bone fractures are generated by breaking a bone and this procedure is recorded using a plurality of updated images. Here, the respective updated images may show the bone in the unbroken state and with varying degrees of bone fracture (for example, single and multiple fractures).

In addition, respective imaging parameters may be assigned to the test images (see the aforementioned). Based on both the test images and the respective imaging parameters, the artificial neural network may then be trained. The artificial neural network may be trained using the test images and the relevant imaging parameters to use imaging parameters of the updated image to generate the three-dimensional subsequent image.

The updated images, (e.g., X-ray images), from earlier imaging examinations may be used in each case to represent the respective bone fracture in different stages, that is, in the untreated state, during intermediate acts in a respective surgical intervention and after completion of the respective surgical intervention.

The simulated updated images, (e.g., simulated X-ray images), may be simulated or generated using, for example, a three-dimensional representation of the bone fracture. The three-dimensional representation of the bone fracture may be a computed tomography image. Using the computed tomography image, a two-dimensional projection of the respective simulated updated images is possible in a particularly simple and comprehensive manner. In this way, particularly large data volumes of simulated updated images may be generated at low cost. The simulated updated images may be generated using a plurality of three-dimensional representations of the bone fracture, with a plurality of three-dimensional representations showing the bone fracture at different stages, for example, in the unbroken state and with varying degrees of bone fracture.

As a result of the fact that the test images represent respective updated images of different degrees of bone fracture and of an unbroken or completely treated bone, the artificial neural network may additionally learn in what way the bone fracture is being treated in the context of the surgical intervention. Changes in position of bone fragments and/or medical objects may be detected and/or interpreted by the artificial neural network particularly well in this way. In this way, the three-dimensional subsequent image may be generated in a particularly reliable manner. Overall, the various methods for providing test images demonstrate how comprehensive and reliable test data may be provided to train the artificial neural network.

According to a development, provision is made for the artificial neural network to be specifically trained in the body region that is to be examined. For example, respective artificial neural networks are trained for different body regions. The artificial neural network trained for the present body region may be selected as a function of the present body region that is to be examined. For example, the body region is a knee, a shinbone, an arm joint, an arm bone, or a shoulder. The artificial neural network may then be specifically trained in one of the body regions listed by way of example in the aforementioned. In this way, prior knowledge to generate the three-dimensional subsequent image may be particularly well configured to the body region that is to be examined.

A second aspect of the disclosure relates to a medical imaging device for performing an imaging examination. The medical imaging device includes: a providing unit to provide an original image of a body region; an imaging unit to record an updated image of the body region; and an artificial neural network trained according to the intended use to generate a three-dimensional subsequent image from the original image and the updated image. The medical imaging device is advantageously set up to carry out a method for performing an imaging examination, which method includes features described in the context of the present disclosure. The providing unit may include a memory for storing the original image and/or a receiving unit for receiving the original image. For example, the medical imaging device is embodied to record the original image using the imaging unit and/or to receive the original image from a further medical imaging device. The medical imaging device is, in particular, a mobile X-ray device, (e.g., a C-arm device).

The features of the method for operating a medical imaging device that are disclosed in the context of the present disclosure therefore also further form the present medical imaging device. In particular, the medical imaging device includes the respective devices or mechanisms that are set up to implement process acts and features of the method.

BRIEF DESCRIPTION OF THE DRAWINGS

The present disclosure is now described in greater detail with the aid of a plurality of drawings, in which.

DETAILED DESCRIPTION

Figure 1:
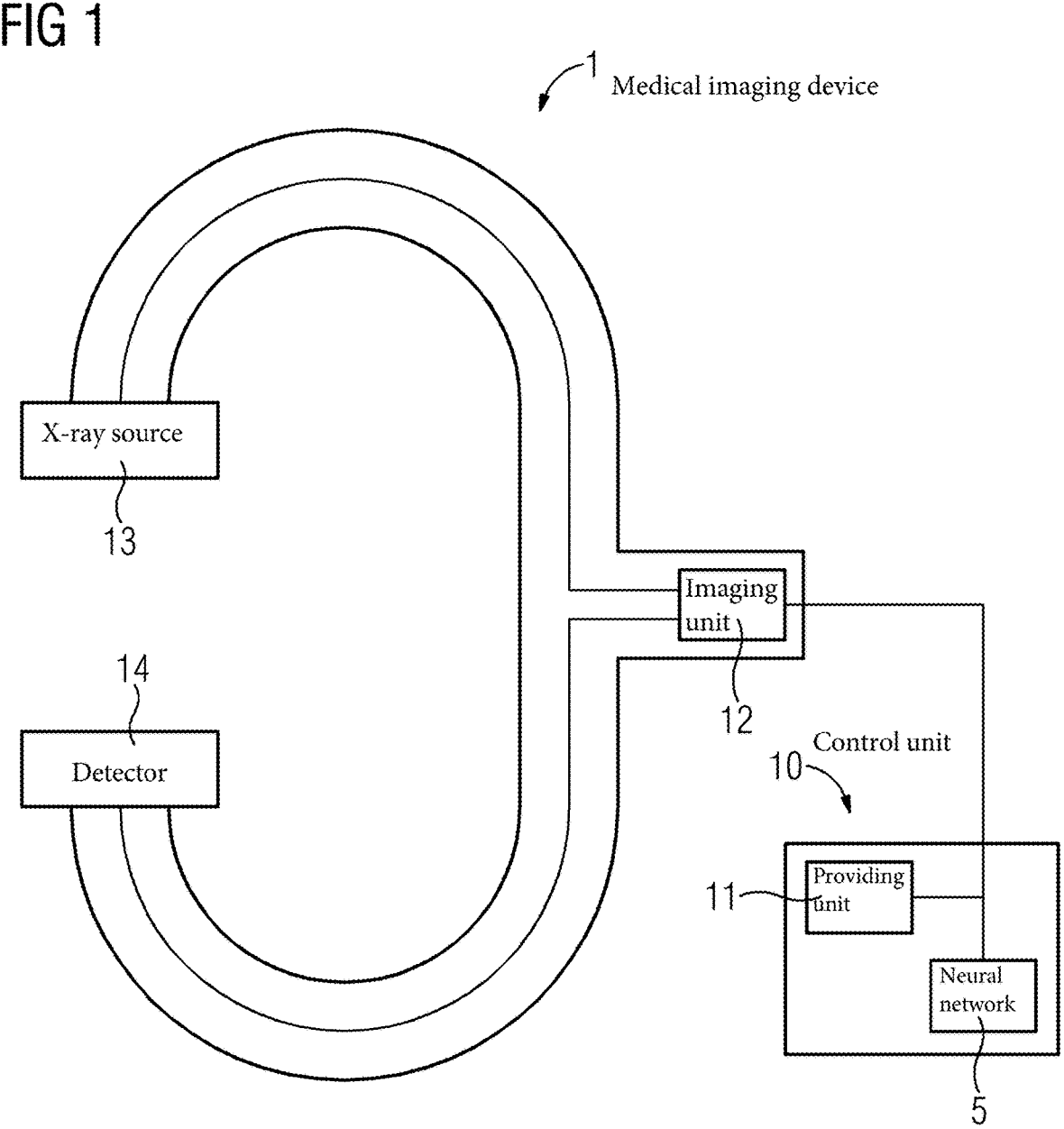
FIG. 1 depicts a schematic view of an example of a medical imaging device.

FIG. 1 depicts a medical imaging device 1, in the present example what is known as a C-arm X-ray device. The imaging device 1 includes, in the present example, an X-ray source 13 and a detector 14. In addition, the imaging device 1 includes an imaging unit 12 to record updated images 3. The updated images 3 in the present exemplary embodiment are X-ray images. In addition, the imaging device 1 has a control unit 10 with a providing unit 11 and an artificial neural network 5. In an operational state of the medical imaging device 1, the artificial neural network 5 is trained according to the intended use.

If the medical imaging device 1 is brought into a relative position according to the intended use with regard to the patient who is to be examined, then an updated image 3 of a body region of the patient may be recorded.

Figure 2:
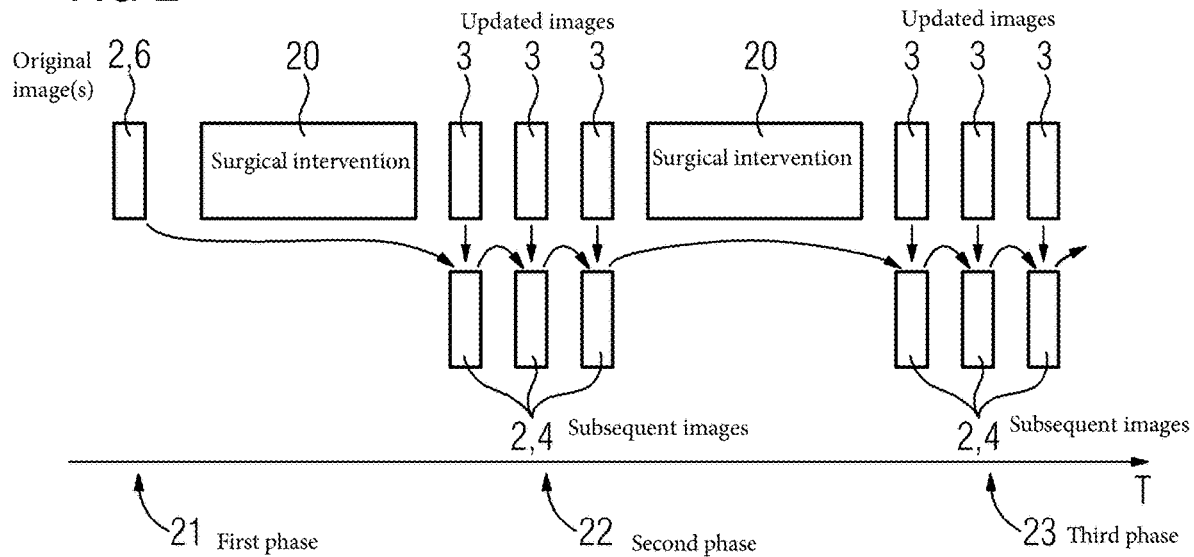
FIG. 2 depicts a schematic overview of a chronological sequence of an exemplary embodiment.

FIG. 2 depicts an exemplary chronological sequence of a method for operating the medical imaging device 1. The respective updated images 3 are recorded during respective different phases 22, 23, 24 with regard to a surgical intervention 20. The different phases 22, 23, 24 relate to the same surgical intervention 20. The surgical intervention 20 is likewise shown on a time chart T but does not form part of the present method. The surgical intervention 20 may be intended, for example, to treat a bone fracture in the patient who is to be examined. A state of the bone fracture and/or of the treatment of the bone fracture may be determined or checked by an imaging examination. Phases 22, 23, 24 may be intermediate phases in the surgical intervention 20. The updated images 3 are recorded in the present case by the medical imaging device 1 during the respective intermediate phases in the surgical intervention 20. In a first phase 21 before the start of the actual surgical intervention 20, in what is known as a preliminary examination phase, either one three-dimensional original image 2 or a plurality of two-dimensional original images 2 are generated or recorded. To distinguish them from later original images 2, the original image 2 or the original images 2 from the first phase 21 are denoted as first original image 6 or first original images 6. By the original images 2 and the updated images 3, the present method allows an improved overview of the body region. The surgical intervention 20 is explicitly not part of the present method.

In the case of a three-dimensional first original image 6, this may be recorded using a computed tomography device. In this case, the imaging device 1 or the providing unit 11 receives the first original image 6 from the computed tomography device. Here the reception may also occur indirectly, for example, via a data carrier for intermediate storage. For this purpose, the providing unit 11 may include an interface, for example, a USB connection or a network connection. In the case of a plurality of first original images 6, these images may be recorded using the imaging device 1. Yet, even in the case of a plurality of first original images 6, these may be received by a further imaging device. In the present case, the plurality of original images 6 are respective two-dimensional X-ray images, which are recorded using the imaging unit 12. The first original images 6 or the first original image 6 may be received by the providing unit 11 from the imaging unit 12 and intermediately stored. The first phase 21 may be a preliminary examination that is carried out shortly before the start of the surgical intervention 20. In other words, the surgical intervention 20 may ensue directly following the first phase 21. The first original images 6, or the first original image 6 therefore characterize the body region at the start of the surgical intervention 20.

In the context of the preliminary examination in the first phase 21, a suitable entry point for the surgical intervention 20 may be determined.

A second phase 22 may interrupt or pause the surgical intervention 20 from a chronological viewpoint. During the second phase 22, a plurality of updated images 3, (e.g., X-ray images), of the body region are recorded using the imaging unit 12. From each of the updated images 3, and from a previous original image 2, a three-dimensional subsequent image 4 is generated iteratively. Here, the subsequent image 4 that is generated is used in each case as an original image 2 to generate the next subsequent image 4. This is visible from the arrows in FIG. 2. To be specific, a first of the subsequent images 4 is generated from the first original image 6 or from the first original images 6 and from a first of the updated images 3. A second of the subsequent images 4 is generated from a second of the updated images 3 and from the first of the subsequent images 4. The first of the subsequent images 4 is therefore used as the original image to generate the second of the subsequent images 4. The details "first" and "second" are to be understood here in relation to the time axis T. The second of the subsequent images 4 therefore characterizes the body region at a later time than the first of the subsequent images 4.

Figure 3:
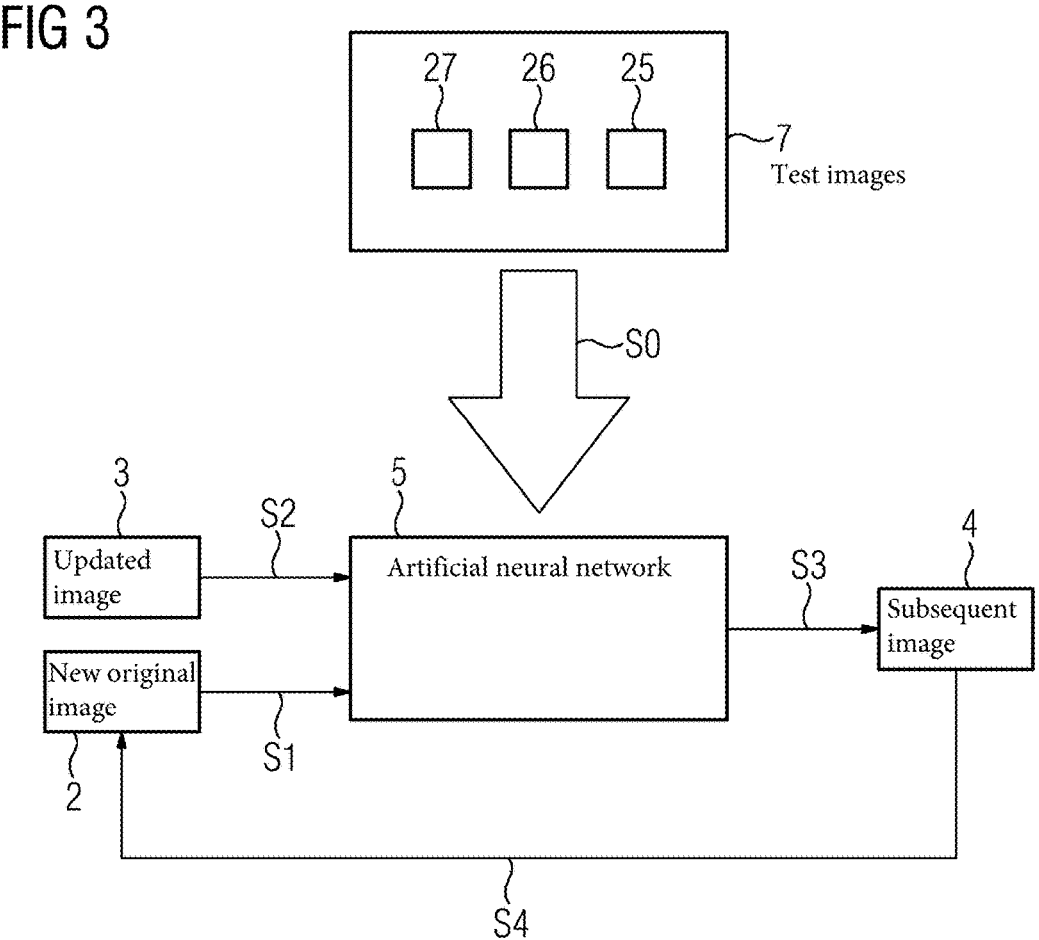
FIG. 3 depicts a flow chart of the exemplary method.

This is also shown in FIG. 3. In act S1, the respective original image 2 is provided for the artificial neural network 5. The artificial neural network has been trained in previous act S0, which is explained in even greater detail hereinafter. In act S2, a respective updated image 3 is recorded and supplied to the artificial neural network 5. In act S3, the artificial neural network 5 generates the respective subsequent image 4 from the original image 2 and the updated image 3. In iteration act S4, the three-dimensional subsequent image 4 that has been generated is used as a new original image 2. The new original image 2 may in turn be supplied with a new updated image 3 to the artificial neural network 5 to generate a new subsequent image 4.

After the second phase 22, the surgical intervention 20 may be continued (FIG. 2). After completion of the surgical intervention 20, there follows a third phase 23. The updated images 3 in the third phase 23 therefore characterize the body region at the end of the surgical intervention 20. The updated images 3 in the second phase 22 characterize the body region during an intermediate phase of the surgical intervention 20. The generation of three-dimensional subsequent images 4 in the third phase 23 ensues in a similar way to the generation of three-dimensional subsequent images 4 in the second phase 22. During generation of the first subsequent image 4 for one of the phases 22, 23, the original image 2 from the respective previous phase 21, 22 is used. To generate the first subsequent image 4 for the second phase 22, the first original image 6 or the first original images 6 from the first phase 21 are used. To generate a first of the subsequent images 4 for the second phase 23, a subsequent image 4 from the second phase 22 is used as the original image 2. Therefore, the subsequent image 4 in the aforementioned cases is generated in each case from an original image 2 and in each case from an updated image 3 which characterize the body region during the various phases of the surgical intervention 20.

During the surgical intervention 20, structural changes to the body region may occur. In the case of a bone fracture, such a structural change may result, for example, through a change in position of a bone fragment and/or of a medical object in the body region. For example, during the surgical intervention 20, bone fragments for treating the bone fracture may be moved relative to one another or be aligned with one another. Alternatively, or additionally, in the context of the surgical intervention 20, medical objects may be arranged or moved in the body region. Examples of medical objects are clamps, screws and pins to fix the bone fragments in place. With reference to the time axis T in FIG. 2, it is possible, for example, between the first phase 21 and the second phase 22 in the context of the medical intervention to provide an alignment of the bone fragments with one another. Here, the bone fragments may be reassembled by the physician carrying out the treatment. The insertion of the medical objects to fix the bone fragments in place may be provided between the second phase 22 and the third phase 23. The moving of the bone fragments and fixing in place of said fragments is expressly not part of the present method. The present method makes it possible, however, to prepare the progress of the movement of the bone fragments and/or alignment of the medical objects visually for the physician carrying out the treatment. Here, the physician carrying out the treatment may be provided with a three-dimensional representation of the body region in the form of the subsequent images 4. The three-dimensional subsequent image 4 may be the three-dimensional representation of the body region. In particular, updated images 3, which have been recorded in different phases 22, 23, 24 of the surgical intervention 20, are used to create the three-dimensional subsequent image 4. In other words, the three-dimensional subsequent image 4 may be formed from updated images 3, which have been recorded in the different phases 22, 23, 24 of the surgical intervention 20.

To allow the generation of the three-dimensional subsequent images 4 using the artificial neural network 5, the artificial neural network first is trained in act S0. Here, prior knowledge is generated by the artificial neural network, due to which the artificial neural network is in a position to generate the three-dimensional subsequent image 4. Without the generation of this prior knowledge, the generation of the three-dimensional subsequent image 4 is not easily possible, because, in the event of few updated images 3 or updated images that deviate considerably from one another 3 (due to structural changes in the context of the surgical intervention 20), an under-determined system may be involved. The term "under-determined" means that too few different projection directions have been provided by the updated images 3. This under-determination of the present system of updated images and original images may be compensated for by the prior knowledge of the artificial neural network. The prior knowledge of the artificial neural network 5 advantageously relates to structures typical of the body region. This is based on the consideration that certain body regions show great similarities in a plurality of people.

The training of the artificial neural network 5 ensues using training data, which includes test images 7. The training data or test images 7 may include simulated updated images 25, updated images 26 of earlier surgical interventions or from earlier imaging examinations, and updated images 27 of artificially broken bones from bodies that have been released for medical research or development. The three-dimensional representations for generating the simulated updated images 25 may be provided by computed tomography. For example, such computed tomography is carried out on artificial fractures for the updated images 27 or using earlier imaging examinations.

With the various updated images 25, 26, 27, it is advantageous in each case if a respective bone fracture is represented by the respective updated images 25, 26, 27 in various stages. The various stages may relate to a non-fractured bone, to a single-fractured bone, and a multiple-fractured bone or to different degrees of dislocation of bone fragments. For example, respective sets of updated images 25, 26, 27 are generated for a non-fractured bone or for a bone that has been reset, for a single-fractured bone and a multiple-fractured bone or for different degrees of dislocation of bone fragments. In this way, the artificial neural network 5 may also be trained with respect to a progression of structural changes in the body region in the course of the surgical intervention 20.

The training data or the test images 7 may be specific to a particular body region. Therefore, the artificial neural network 5 may be trained specific to a particular body region. Examples of body regions that may be represented by the training data or the test images 7 and for which the artificial neural network 5 may be trained are: knee, shinbone, arm-joint or crook of the arm, the bone of the forearm, and the shoulder. This list is not intended to be restrictive. To carry out the imaging examination, an artificial neural network 5 specific to the examination of the body region may be selected from a plurality of artificial neural networks.

Provision is made for the artificial neural network 5 to determine structural changes in the body region that have occurred between the original image 2 and the updated image 3. To generate the three-dimensional subsequent image 4, such a structural change is accounted for. This is accounted for, in particular, by determining changes in position of bone fragments and/or of medical objects between the original image 2 and the updated image 3. If such a change in position has occurred, then this is accounted for by moving a representation of the respective bone fragment or of the respective medical object in the original image 2. In other words, the representation of a bone fragment or of a medical object in the original image may be moved by the artificial neural network 5 if a position of the respective bone fragment and/or of the medical object in the updated image 3 has changed. This may be interpreted as a movement compensation, in which a movement of the bone fragment and/or of the medical object is compensated for by moving the respective representation in the original image 2. In this way, a position in which the bone fragment or the medical object is represented in the original image 2 may be adjusted to match the more up to date updated image 3.

Overall, the exemplary embodiment demonstrates how an improved representation of a body region may be provided in the form of the three-dimensional subsequent image.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for operating a medical imaging device when performing an imaging examination, the method comprising:
   providing an original image of a body region;
   recording an updated image of the body region; and
   generating a three-dimensional subsequent image from the original image and the updated image using a previously trained artificial neural network.

2. The method of claim 1, wherein the original image is a three-dimensional original image of the body region.

3. The method of claim 1, wherein the updated image represents the body region at a later time than the original image.

4. The method of claim 1, wherein the original image is generated in a context of computed tomography, and
wherein the recording of the updated image uses a mobile X-ray device,
wherein the mobile X-ray device is a C-arm X-ray device.

5. The method of claim 1, wherein, in the generation of the three-dimensional subsequent image, the original image of the body region is at least partly updated using the updated image.

6. The method of claim 1, wherein the original image and the updated image characterize the body region during different phases of a same surgical intervention.

7. The method of claim 6, wherein the artificial neural network is trained specifically in one phase of the different phases.

8. The method of claim 1, wherein a structural change in the body region, which has occurred between the original image and the updated image, is determined and accounted for in the generation of the three-dimensional subsequent image.

9. The method of claim 8, wherein a change in position of a bone fragment and/or of a medical object is determined in the body region as the structural change.

10. The method of claim 9, wherein, to account for the structural change, the change in position of the bone fragment and/or of the medical object is determined and is accounted for by moving a representation of the bone fragment or the medical object in the original image.

11. The method of claim 1, wherein a plurality of original images is provided and/or a plurality of updated images is recorded, and
wherein the three-dimensional subsequent image is generated from the plurality of original images and/or the plurality of updated images.

12. The method of claim 1, wherein the artificial neural network is at least partly trained using test images, and
wherein the test images comprise updated images of bone fractures from earlier imaging examinations and/or simulated updated images generated using a three-dimensional representation of a bone fracture.

13. The method of claim 1, wherein the artificial neural network is trained specifically in the body region that is to be examined.

14. A method for operating a medical imaging device when performing an imaging examination, the method comprising:
providing an original image of a body region;
recording an updated image of the body region; and
iteratively generating a three-dimensional subsequent image from the original image and the updated image using a previously trained artificial neural network,
wherein, in an iterative generation, the three-dimensional subsequent image is used as a new original image and a new three-dimensional subsequent image is generated together with a new updated image.

15. A medical imaging device for performing an imaging examination, the medical imaging device comprising:
a providing unit configured to prepare an original image of a body region;
an imaging unit configured to record an updated image of the body region; and
a trained artificial neural network configured to generate a three-dimensional subsequent image from the original image and the updated image.

* * * * *